(12) United States Patent
McCrary et al.

(10) Patent No.: US 8,798,709 B1
(45) Date of Patent: Aug. 5, 2014

(54) DERMAL SENSING PACKAGE AND USE

(75) Inventors: Craig R. McCrary, Valencia, CA (US);
David A. Sheraton, Sr., San Clemente, CA (US); Joana Lavinia Prunean, La Habra, CA (US)

(73) Assignee: Neotech Products, Inc., Valencia, CA (US)

( * ) Notice: Subject to any disclaimer, the term of this patent is extended or adjusted under 35 U.S.C. 154(b) by 298 days.

(21) Appl. No.: 12/799,060

(22) Filed: Apr. 19, 2010

(51) Int. Cl.
*A61B 5/0408* (2006.01)

(52) U.S. Cl.
USPC .......................................... 600/392; 600/391

(58) Field of Classification Search
CPC ... A61B 5/0487; A61B 5/0478; A61B 5/0492
USPC .................................................. 600/391, 392
See application file for complete search history.

(56) References Cited

U.S. PATENT DOCUMENTS

| 4,239,046 | A | * | 12/1980 | Ong | 600/391 |
| 4,458,696 | A | * | 7/1984 | Larimore | 607/152 |
| 5,265,579 | A | * | 11/1993 | Ferrari | 600/385 |
| 5,824,033 | A | * | 10/1998 | Ferrari | 607/142 |
| 6,418,333 | B1 | * | 7/2002 | Axelgaard | 600/391 |
| 6,731,965 | B2 | * | 5/2004 | Menon et al. | 600/396 |
| 6,795,722 | B2 | * | 9/2004 | Sheraton et al. | 600/391 |
| 7,697,998 | B2 | * | 4/2010 | Axelgaard | 607/142 |
| 8,116,841 | B2 | * | 2/2012 | Bly et al. | 600/391 |

* cited by examiner

*Primary Examiner* — Lee S Cohen
(74) *Attorney, Agent, or Firm* — William W. Haefliger

(57) ABSTRACT

A sensor apparatus in the form a substantially flat package for receiving and transmitting physiologic electronic signals, to be monitored or recorded, comprising in combination, a first layer consisting of hydrogel and having opposite ends, second layer sections projecting oppositely relative to the opposite ends, and consisting of hydrocolloid, a thin conductive third layer directly overlying and contacting the top of the first layer, an electrical lead in contact with the thin conductive layer, and extending to the exterior of the layers, there being phthalate-free insulation on said lead, adhesive adhering the lead to said thin conductive layer, and a cover layer extending over the first, second and third layers, and over the lead.

13 Claims, 2 Drawing Sheets

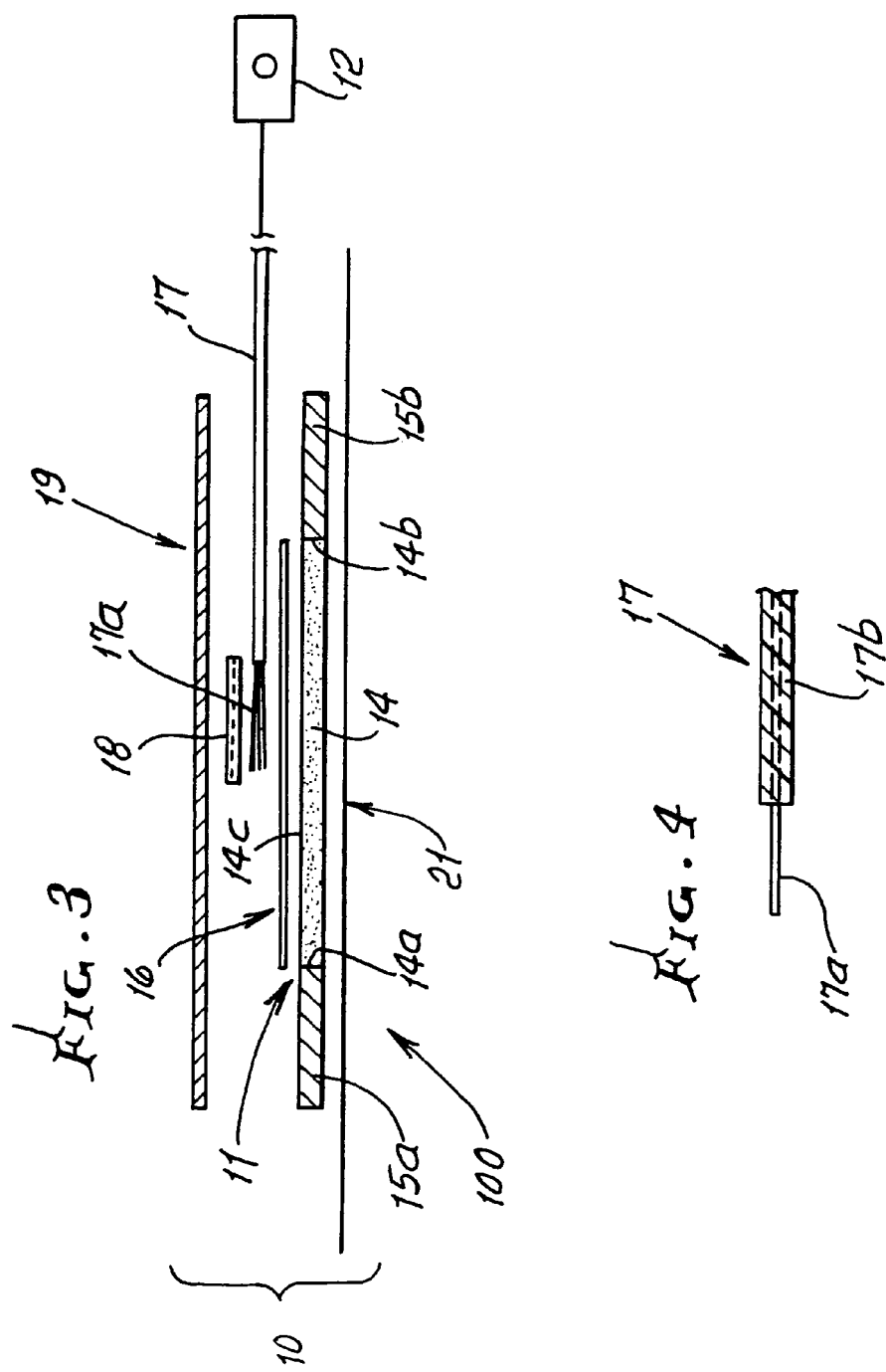

DERMAL SENSING PACKAGE AND USE

BACKGROUND OF THE INVENTION

This invention relates generally to sensors attachable to the skin of a patent, such as an infant, and more particularly to improvements in sensor packages for topically receiving and transmitting physiologic signals such as cardiac rhythm, brain wave and other electronic signals.

There is need for improvements in such sensors, particularly as related to achieving flat package configurations, improved adhesion to fragile skin, protection of electrical components, via the skin, in a non-invasive manner, for monitoring or recording, and ease and reliability of use, as well as other objectives and advantages in construction as will be seen.

There is also need for skin applicable sensor devices incorporating the unusual advantages in structure, function and results as are now provided by the present invention.

SUMMARY OF THE INVENTION

It is a major object of the invention to provide improvements in such sensor packages and their uses meeting the above needs.

Basically, the sensor package of the invention comprises, in combination:

a) a first layer consisting of hydrogel and having opposite ends, b) second layer sections projecting oppositely relative to said opposite ends, and consisting of hydrocolloid, and c) a thin conductive third layer directly overlying and contacting the top of the first layer, d) an electrical lead in contact with said thin conductive layer, and extending to the exterior of such layers, there being phthalate-free insulation on lead wiring, e) adhesive adhering the lead to the thin conductive layer, f) and, a cover layers extending over the first, second and third layer, and over said lead.

Additional objects includes providing the third layer to consist of carbon with extensive surface contact with the first layer, the electrical lead held in electrical surface contact with the third layer, as by adhesive material; provision of a release liner extending at the bottom surface of the first layer and the second layer sections, and adhered thereto; provision for radiolucent properties of the first, second and third layers; and wherein all of the insulation on the lead wiring is phthalate-free; and the insulation on the lead wiring typically consists of PVC.

Additional unusual advantages include:

Hydrocolloid ends and center or/of intermediate hydrogel provide:

Excellent electronic tracings;

Long term adhesion (several days) to the patient. (Prior electrodes last less than Prevention of fall off prematurely, under moist or humid conditions;

Combinations of different adhesives provides ideal properties when under high humidity (hydrogel has a strong initial tact, while hydrocolloid provides the long term adhesion to skin.

Hydrocolloid on ends of hydrogel, prevents gel from oozing out.

Can be placed on human limbs, without having to be secured by a strap that wraps around the limb;

Small size, allows for sensor placement on the limbs or the body of the infant.

Small size leaves more body area open for other products to be secured.

All materials of the package are radiolucent, and will not appear on an X-ray.

Device does not need to be removed during X-ray procedure;

Lead wires are phthalate free.

These and other objects and advantages of the invention, well as the details of an illustrative embodiment, will be more fully understood from the following specification and drawings, in which:

DRAWING DESCRIPTION

FIG. 3 is an exploded view of components of a preferred package; and

FIG. 4 is a view showing wiring, with phthalate-free insulation.

DETAILED DESCRIPTION

Figure 1:
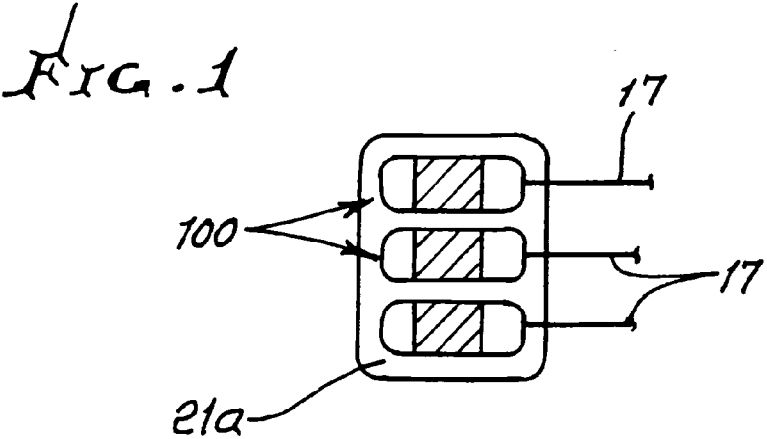
FIG. 1 is a plan view of a group of packages.

In the drawings, the sensor apparatus 10 is shown in the form of a substantially flat package 11 for receiving and transmitting signals, to be monitored or recorded, as at 12.

In FIG. 3, the package 100 is shown to include:

a) a first layer 14 consisting of hydrogel and having opposite ends 14a and 14b, b) second layer sections 15a and 15b projecting endwise oppositely relative to layer 14 opposite ends, and consisting of hydrocolloid, c) a thin conductive third layer 16 directly overlying and contacting the top 14c of the first layer, d) an insulated electrical lead 17 with end wires 17a in contact with the thin conductive layer 16, and extending to the exterior of all layers;

e) adhesive liquid 18 adhering the end wires to the thin conductive layer 16, as at its top surface 16a, f) and an insulative cover layer 19 extending over said first, second and third layers, and over lead 17.

Figure 2:
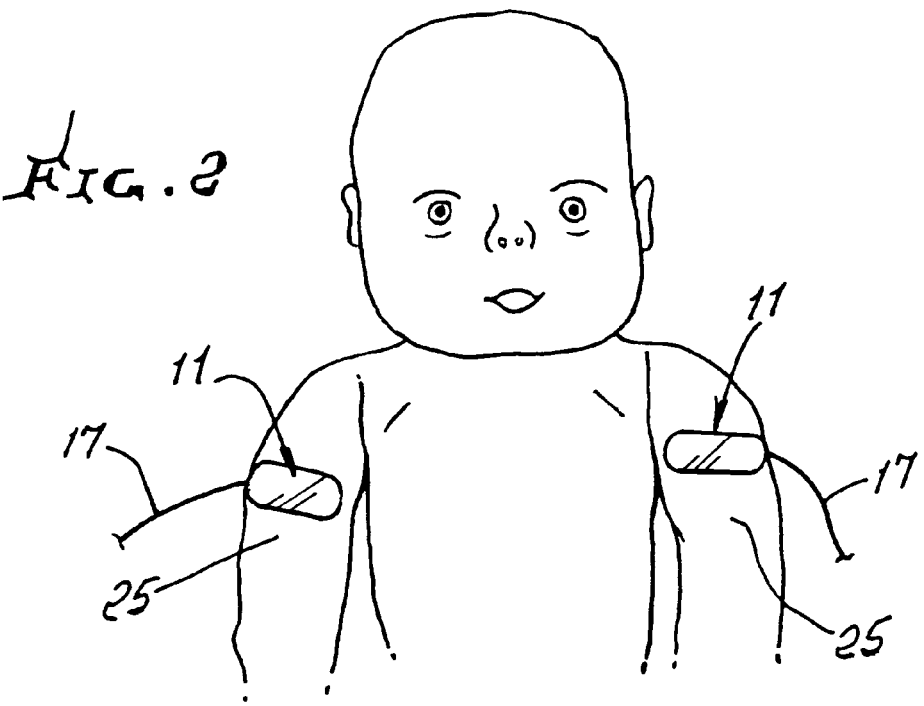
FIG. 2 is an elevation showing attachment of packages to the arm of an infant patient.

In this regard, wires 17a typically consist of carbon, as does thin conductive layer 16, for maximum conductively. Also, cover layer 19 typically consists of non-woven insulative material, and adhesive at its bottom side serves to adhesively adhere to and seal adjacent the tops of 15a and 15b, the lead 17 and wires 17a, and the third layer or pad 16, for enclosing these elements. Lead 17 is firmly anchored to the top of 15b by cover 19. A visibly clear release liner 21 covers the bottom surfaces of 14, 15a and 15b, to be stripped off when the package is to be adhered via bottom surfaces of 14 and 15, to the infant's skin, such as in its arms 25 as shown in FIG. 2. All layers are radiolucent.

As seen in the drawings, the first layer and said second layer sections having coplanar bottom surfaces define a continuous tacky lower surface engaging said release liner.

A group of the elongated packages 100 is shown in FIG. 1 as carried to extend in parallel on a common enlarged release liner 21a, to be pulled free of that liner, for use. Bottom surfaces of 14 and 15 are tacky to adhere to an infant's skin. Note typical dimensions, in inches, of elements shown, indicative of small size, and releasability from the liner 21a, for use.

As shown in FIG. 4, the lead 17 comprises insulation 17b covering electrically conductive wiring 17a. The insulation is phthalate-free, and typically consists of PVC. Phthalates, although useful as plasticizers, are considered as harmful, or potentially harmful to health, and particularly to infants.

We claim:

1. A sensor apparatus in the form a substantially flat package for receiving and transmitting electronic signals, to be monitored or recorded, comprising in combination:
   a) a first horizontal layer consisting of hydrogel and having opposite ends,
   b) a second layer co-planar with the first layer and having spaced apart sections projecting horizontally endwise oppositely relative to first layer opposite ends, and consisting of hydrocolloid, said sections being in endwise contact with said first layer opposite ends, and defining junctions therewith, said first and second layers having the same thickness, at said junctions whereby said opposite ends of the first layer are everywhere adjacently enclosed by ends of said second layer eliminating all open space therebetween, the two layers being in adjacent end-to-end contact throughout the thicknesses of both layers,
   c) a thin electrically conductive horizontally extending third layer directly overlying and having extensive surface to surface contact with the top of the first layer, and located above the level of the second layer said third layer being a single layer having everywhere the same total thickness which is substantially less than the thickness of each of the first and second layers, all of the first layer being directly below the third layer, said third layer having opposite ends that extend to said junctions of said first layer opposite ends with said second layer sections,
   d) an electrical lead in contact with the top of said thin conductive layer, and extending horizontally to the exterior of said layers, there being phthalate-free insulation on said lead, said third layer being the only layer between said lead and said first layer,
   e) adhesive adhering end wires of the lead to the top of said thin conductive layer,
   f) a protective cover layer which is insulative extending over said first, second and third layers, and over said lead,
   g) release liner extending at the bottom surfaces of the first layer and the second layer sections, and adhered thereto,
   h) said first layer and second layer sections having co-planar bottom surfaces defining a continuous tacky lower surface engaging said release liner,
   i) and said first layer and second layer sections having co-planar top surfaces defining a continuous upper surface, the top surface of the first layer engaged by said third layer between said first layer opposite ends, said first, second and third layers being radiolucent,
   j) said first, second and third layers located at the underside of the lead.

2. The combination of claim 1 wherein said third layer consists of carbon having thickness everywhere less than the thickness of each of the first and second layers.

3. The combination of claim 1 wherein said lead extends over and is anchored to one of said second layer sections.

4. The combination of claim 1 wherein the release liner is enlarged and carries multiple packages, which are elongated and extend in parallel relation, for individual pull-off release in a common direction.

5. The combination of claim 1 wherein the first layer is rectangular.

6. The combination of claim 4 wherein the first layer of each package is rectangular.

7. The combination of claim 1 wherein the overall length dimension of the first and second layers is about 1 inch.

8. The combination of claim 7 wherein the overall width dimension of said first and second layers is about 0.38 inch.

9. The combination of claim 8 wherein the release liner supports at least three packages.

10. The combination of claim 1 wherein said insulation covers lead wiring that is electrically conductive.

11. The combination of claim 10 wherein said insulation comprises PVC.

12. The combination of claim 1 wherein said insulation consists essentially of PVC.

13. The combination of claim 1 wherein all of the insulation in or on said package is phthalate-free.

* * * * *